United States Patent
Davidson et al.

(10) Patent No.: US 7,067,124 B2
(45) Date of Patent: Jun. 27, 2006

(54) PROTEASE COMPOSITION AND METHOD FOR TREATING A DIGESTIVE DISORDER

(75) Inventors: John G. Davidson, Kissee Mills, MO (US); Rohit Medhekar, Springfield, MO (US); Jeremy Moore, Springfield, MO (US); Ken Paydon, Forsyth, MO (US); Steve Marr, Forsyth, MO (US)

(73) Assignee: National Enzyme Company, Forsyth, MO (US)

( * ) Notice: Subject to any disclaimer, the term of this patent is extended or adjusted under 35 U.S.C. 154(b) by 497 days.

(21) Appl. No.: 10/249,303

(22) Filed: Mar. 28, 2003

(65) Prior Publication Data

US 2004/0191237 A1    Sep. 30, 2004

(51) Int. Cl.
*A61K 38/54* (2006.01)

(52) U.S. Cl. .................. 424/94.2; 424/94.6; 424/94.63
(58) Field of Classification Search ............... 424/94.2, 424/94.63, 94.6
See application file for complete search history.

(56) References Cited

OTHER PUBLICATIONS

Merriam Webster Online Dictionary "prevent" http://m-w.com/dictionary/preventing.*

* cited by examiner

*Primary Examiner*—Jean C. Witz
(74) *Attorney, Agent, or Firm*—Joseph A. Mahoney; Mayer, Brown, Rowe & Maw LLP

(57) ABSTRACT

There is provided methods, kits, combinations, and compositions comprising a *Aspergillus oryzae* protease enzyme, a *Bacillus subtilis* protease enzyme, and a *Aspergillus niger* lipase enzyme for treating a digestive disorder in a subject in need thereof. The methods, kits, combinations, and compositions may also be used along with an agent (or combination of agents) for raising the gastric pH, a digestive enzyme useful in enhancing digestive activity, a dietary supplement, or a pharmaceutical agent.

43 Claims, No Drawings

PROTEASE COMPOSITION AND METHOD FOR TREATING A DIGESTIVE DISORDER

BACKGROUND OF INVENTION

Digestion of food begins in the mouth, continues in the stomach and is completed in the small intestine. Saliva contains an enzyme called ptyalin, an a-amylase, which begins the process of digestion by breaking down carbohydrates. Ptyalin remains active in the stomach and continues its digestion of carbohydrates until acid is produced in the stomach and gastric pH decreases. Along with acid, the stomach also produces an enzyme known as pepsin. Pepsin is a protease, which digests proteins. Pepsin is only active at the low pH of the stomach. The partially digested mixture then moves into the small intestine where the acid is neutralized by bicarbonate and the pH elevates to neutral. The various proteases, carbohydrases and lipases produced by the pancreas and the cells of the small intestine then further break down the partially digested food into a form that can be absorbed by the body. This is the ideal digestive process. However, most people occasionally suffer from some kind of digestive disorder. The most commonly occurring digestive problems are heartburn, indigestion and flatulence.

Heartburn and other maladies caused by the acid in the stomach can be a mild annoyance, or they can be a sign of a pathological disorder, such as gastroesophageal reflux disease (GERD). Gastroesophageal reflux occurs when the stomach contents, particularly the acid, move up into the esophagus, and is usually caused by a weakened lower esophageal sphincter. Though this condition can be caused by an abnormality in the esophageal sphincter, frequently it results from external factors. Certain foods can cause the sphincter to relax, and obesity puts excess pressure on the sphincter, which can cause or worsen the condition. The lining of the esophagus is not equipped to resist the corrosion caused by the acid and slowly erodes. If left untreated this erosion can lead to esophageal cancer.

However, digestive problems can result from many other factors as well. The consumption of too many fatty foods, physical and emotional stress, smoking, alcohol, other health conditions, exposure to pollution and pathogens, amount of exercise, and the amount and type of food consumed can all contribute to digestive disturbances. Any situation that impedes the secretion of stomach acid and bicarbonate, or the release of the proper digestive enzymes can negatively impact digestion.

There are numerous medications available that can effectively treat heartburn and indigestion. Medications useful in treating heartburn are antacids and H2 blockers. Antacids, which are mostly calcium carbonate, magnesium hydroxide, aluminum hydroxide, and/or sodium bicarbonate tablets, work by neutralizing the acid produced in the stomach. On the other hand, H2 blockers are drugs that inhibit the production of acid in the stomach. Both types of medication are effective in treating heartburn and usually eliminate symptoms within a short period of time.

Pepsin, as mentioned earlier, is a protease produced in the stomach that is activated by the acid in the stomach. Pepsin is active in a very narrow pH range, pH 1 3. This enzyme loses activity very rapidly above pH 3 and is inactive at a pH of more than 3.5. Antacids and H2 blockers relieve symptoms of heartburn by raising the pH of the stomach. Experiments have shown that the pH of the stomach is raised to between 5 and 6 when antacids are administered. At that high pH level pepsin is rendered inactive consequently halting protein digestion in the stomach. It has escaped mainstream attention that the near-epidemic use of antacids in the U.S. brings some consequence. Apart from the disturbance of normal human gut microbial flora, raising the pH of the gastric environment renders the endogenous proteolytic enzyme pepsin inactive. This unintended effect, in turn, may exacerbate one of the potential underlying conditions of indigestion: pancreatic insufficiency.

For these and other reasons, therefore, it would be a difficult but much desired advance in the art to provide effective methods, kits, combinations, and/or compositions for supplementing the activity of internally produced digestive enzymes. Supplemental digestive enzymes can alleviate the problem of poor digestion due to poor internal production of digestive enzymes, and enable enhanced absorption of nutrients from ingested food from the digestive tract.

Fungal proteases have a broad pH range and work in acidic as well as neutral environments. As shown below, a combination of fungal and bacterial proteases and fungal lipases, with either antacids or $H_2$ blockers are not only effective in relieving heartburn but also ensure that protein and fat digestion continues in the stomach.

As hereinafter described, the present invention is an improvement over the disclosures of U.S. Pat. Nos. 6,013, 680 and 5,629,013.

FIELD OF THE INVENTION

The present invention is related to methods, kits, combinations, and compositions for treating a digestive disorder in a subject in need thereof with a digestive enzyme.

SUMMARY OF INVENTION

The present invention is directed to a composition, comprising: (a) at least one protease; (b) at least one lipase; and (c) an antacid. The composition may be prepared in the form of tablets, capsules, powders, solutions, suspensions, and troches for oral administration. Alternatively, compositions comprising an antacid plus a protease or lipase are also described herein.

The present invention is also directed to a method for increasing the digestion of protein in the gastrointestinal tract by administering an effective amount of the above composition. Such improved digestion alleviates heartburn, acid indigestion, sour stomach, and other gastrointestinal disorders related to poor protein digestion.

DETAILED DESCRIPTION

The methods, kits, combinations, and compositions of the present invention provide enhanced treatment options for treating a digestive disorder in a subject in need thereof as compared to those currently available.

While the present invention may be embodied in many different forms, several specific embodiments are discussed herein with the understanding that the present disclosure is to be considered only as an exemplification of the principles of the invention, and it is not intended to limit the invention to the embodiments illustrated. Where the invention is illustrated herein with particular reference to an *Aspergillus oryzae* or *Bacillus subtilis* protease enzyme, it will be understood that any other protease enzyme can, if desired, be substituted in whole or in part for the *Aspergillus oryzae* or *Bacillus subtilis* protease enzyme, in the methods, kits, combinations, and compositions herein described. Where the invention is illustrated herein with particular reference to an *Aspergillus niger* lipase enzyme, it will be understood that any other lipase enzyme can, if desired, be substituted in whole or in part for the *Aspergillus niger* lipase enzyme in the methods, kits, combinations, and compositions herein described. Suitable enzymes are identified in ETA's Partial List of Enzymes, which is incorporated herein by reference.

Where the invention is illustrated herein with particular reference to ranitidine, cimetidine, famotidine, nizatidine, and roxatidine acetate, it will be understood that any other histamine $H_2$ receptor antagonist can, if desired, be substituted in whole or in part for such compounds in the methods, kits, combinations, and compositions herein described. Where the invention is illustrated herein with particular reference to omeprazole, lansoprazole, or rabeprazole, it will be understood that any other proton pump inhibiting agent can, if desired, be substituted in whole or in part for such agents in the methods, kits, combinations, and compositions herein described. Where the invention is illustrated herein with particular reference to calcium carbonate, it will be understood that any other antacid, can if desired, be substituted in whole or in part for calcium carbonate in the methods, kits, combinations, and compositions herein described. Such antacids may include sodium bicarbonate, other calcium salts, aluminum salts, and magnesium salts.

The present invention is directed to methods, kits, combinations, and compositions for treating, preventing or reducing the risk of developing a digestive disorder, or the symptoms associated with or related to a digestive disorder, in a subject in need thereof. In one embodiment, the composition comprises an *Aspergillus oryzae* protease enzyme, a *Bacillus subtilis* protease enzyme, an *Aspergillus niger* lipase enzyme, and optionally an agent (or combination of agents) for raising the gastric pH of the subject.

In another embodiment of the present invention, the method comprises administering to a subject in need thereof a digestive-disorder-effective amount of a composition comprising an *Aspergillus oryzae* protease enzyme, a *Bacillus subtilis* protease enzyme, an *Aspergillus niger* lipase enzyme, and optionally an agent (or combination of agents) for raising the gastric pH of the subject, or a digestive enzyme useful in enhancing the digestive activity in the subject.

In another embodiment of the present invention, the method comprises administering to a subject in need thereof a combination therapy of an *Aspergillus oryzae* protease enzyme, a *Bacillus subtilis* protease enzyme, an *Aspergillus niger* lipase enzyme, and optionally an agent (or combination of agents) for raising the gastric pH of the subject, or a digestive enzyme useful in enhancing the digestive activity in the subject.

In yet another embodiment of the present invention, a pharmaceutical composition is made by combining a digestive-disorder-effective amount of a compound that comprises an *Aspergillus oryzae* protease enzyme, a *Bacillus subtilis* protease enzyme, an *Aspergillus niger* lipase enzyme, and optionally an agent (or combination of agents) for raising the gastric pH of the subject, or a digestive enzyme useful in enhancing the digestive activity in the subject; and a pharmaceutically acceptable carrier, excipient, adjuvant, and/or vehicle.

In still another embodiment of the present invention, a method of making a pharmaceutical composition is provided. The method comprises combining a digestive-disorder-effective amount of a compound that comprises an *Aspergillus oryzae* protease enzyme, a *Bacillus subtilis* protease enzyme, an *Aspergillus niger* lipase enzyme, and optionally an agent (or combination of agents) for raising the gastric pH of the subject, or a digestive enzyme useful in enhancing the digestive activity in the subject; and a pharmaceutically acceptable carrier, excipient, adjuvant, and/or vehicle.

Besides being useful for human treatment of a digestive disorder, the present invention is also useful for veterinary treatment of companion mammals, exotic animals, and farm animals, including mammals, birds, rodents, and the like. More particularly, the methods, kits, combinations, and compositions of the present invention are useful for treatment of a digestive disorder in a horse, cow, chicken, pig, dog, or cat.

In another embodiment of the present invention, the *Aspergillus oryzae* protease enzyme, *Bacillus subtilis* protease enzyme, and *Aspergillus niger* lipase enzyme are formulated in a single composition.

In still another embodiment of the present invention, the *Aspergillus oryzae* protease enzyme, *Bacillus subtilis* protease enzyme, and *Aspergillus niger* lipase enzyme are administered in a sequential manner.

In another embodiment of the present invention, the *Aspergillus oryzae* protease enzyme, *Bacillus subtilis* protease enzyme, and *Aspergillus niger* lipase enzyme are administered in a substantially simultaneous manner.

In one embodiment, the amount of *Aspergillus oryzae* protease enzyme, *Bacillus subtilis* protease enzyme, and *Aspergillus niger* lipase enzyme in the methods, kits, combinations, and compositions of the present invention together make a digestive-disorder-effective amount.

In yet another embodiment of the present invention, the method, kit, combination, or composition comprises at least about 500 HUT *Aspergillus oryzae* protease enzyme. In another embodiment of the present invention, the composition comprises about 500 HUT to about 500,000 HUT *Aspergillus oryzae* protease enzyme. In still another embodiment of the present invention, the method, kit, combination, or composition comprises about 8,000 HUT *Aspergillus oryzae* protease enzyme.

In another embodiment of the present invention, the method, kit, combination, or composition comprises at least about 750 PC *Bacillus subtilis* protease enzyme. In another embodiment of the present invention, the composition comprises about 750 PC to about 750,000 PC *Bacillus subtilis* protease enzyme. In yet another embodiment of the present invention, the method, kit, combination, or composition comprises about 3,000 PC *Bacillus subtilis* protease enzyme.

In another embodiment of the present invention, the method, kit, combination, or composition comprises at least about 10 FCCLU *Aspergillus niger* lipase enzyme. In yet another embodiment of the present invention, the composition comprises about 10 FCCLU to about 20,000 FCCLU *Aspergillus niger* lipase enzyme. In yet another embodiment of the present invention, the method, kit, combination, or composition comprises about 100 FCCLU *Aspergillus niger* lipase enzyme.

Although not required, the proteases and lipases of the present invention will preferably have an activity level relating to a pH range useful for the purpose of gastric digestion of proteins in combination with an antacid and the resultant gastric pH conditions. Further, the digestive activity of the present invention is not necessarily restricted to the stomach, but may be sustained throughout the gastrointestinal tract due to the effective pH range of the enzymes used.

The present invention includes methods, kits, combinations, and compositions for reversing, halting, or slowing the progression of a digestive disorder once it becomes clinically evident, or treating the symptoms associated with or related to a digestive disorder. The subject may already have a digestive disorder at the time of administration, or be at risk of developing a digestive disorder.

A kit of the present invention comprises a composition comprising an *Aspergillus oryzae* protease enzyme, a *Bacillus subtilis* protease enzyme, an *Aspergillus niger* lipase enzyme, and optionally an agent for raising gastric pH of the subject, and/or a digestive enzyme useful in enhancing digestive activity in the subject. In one embodiment of the present invention, the *Aspergillus oryzae* protease enzyme, *Bacillus subtilis* protease enzyme, and *Aspergillus niger* lipase enzyme are provided as separate components of a kit. The kit can also contain a set of instructions.

In one embodiment of the present invention, the agent for raising gastric pH of the subject may comprise an antacid, a histamine $H_2$ receptor antagonist, or a proton pump inhibitor.

An antacid neutralizes the otherwise acidic character of the fluid in the gastrointestinal tract. Illustratively, the antacid includes aluminum hydroxide, magnesium aluminosilicate, magnesium silicate, aluminum silicate, hydrotalcite, magnesium oxide, magnesia alumina hydrate, aluminum hydroxide, magnesium hydroxide, sodium bicarbonate, sodium carbonate, magnesium carbonate, calcium carbonate, magnesium aluminometasilicate, anhydrous calcium hydrogenphosphate, calcium lactate, calcium glycerophosphate, and calcium hydrogenphosphate. In one embodiment of the present invention, the antacid is calcium carbonate. In another embodiment, the antacid is aluminum hydroxide or magnesium hydroxide such as Maalox® or Mylanta® antacid, which are available commercially. The dose of antacid administered depends on the particular one used. For example, when the antacid is Mylanta®, between 15 ml and 30 ml is administered to an adult human per dose. Combinations of antacids can be used in the methods, kits, combinations, and compositions herein described.

In still another embodiment of the present invention, the histamine $H_2$ receptor antagonist is ranitidine, cimetidine, famotidine, nizatidine, and roxatidine acetate. The dosage of the $H_2$ receptor antagonist administered depends on the particular one used. For example, when the $H_2$ receptor antagonist is cimetidine or ranitidine, between 200 and 800 mg per day is administered to an adult human in single or divided doses.

In yet another embodiment of the present invention, the proton pump inhibitor comprises omeprazole, lansoprazole, or rabeprazole at doses known in the art.

In still another embodiment of the present invention, the optional digestive enzyme comprises a proteolytic enzyme (protein digestion), a lipolytic enzyme (fat digestion), an amylolytic enzyme (carbohydrate digestion), and/or a cellulase (fiber digestion). Specific classes of digestive enzymes useful in the methods, kits, combinations, and compositions of the present invention include amylase, protease (for example, protease I and II), invertase, maltase, bromelain, cellulase, lipase, sucrase, lactase, or lipase. Other enzyme types useful in the methods, kits, combinations, and compositions of the present invention include alcohol dehydrogenase, alpha-acetoloactate decarboxylase, amino acylase, alpha-amylase, beta-amylase, amylo-glucosidase, bromelain, catalase, cholesterol esterase, collangenase, cyclodextrin gluco transferase, dextranase, deaminase, elastase, alpha-galactosidase, beta-galactosidase, galacto mannanase, beta-glucanase, beta-glucosidase, glucose isomerase, glucose oxidase, gluco transferase, hemicellulase, hyaluronidase, insulinase, invertase (syn. with sucrase), laccase, lacto peroxidase, lipase, lysozyme, 5'-nucleotidease, papain, pentosanase, pectinase, polygalacturonase, peroxidase, phospholipase A2, phospholipase D, phytase, polyphenol oxidase, pronase, proteinase (for example, serine type proteinase, thiol type proteinase, carboxyl-acid type proteinase, microbial metallo type proteinase), pullunase, rennets, tannase, urease, urokinase, and xylanase. These optional digestive enzymes may be from a plant, animal, or microorganism source. Combinations of the above-mentioned enzymes can be used in the methods, kits, combinations, and compositions herein described.

The methods, kits, combinations, and compositions of the present invention are useful in treatment and prevention of a very wide range of digestive disorders, including, for example, upper gastrointestinal tract distress (such as heartburn, indigestion, stomachache, sour stomach), inflammatory bowel disease, gastritis, irritable bowel syndrome, ulcerative colitis, dairy intolerance, gallbladder stress, malabsorption, intestinal toxemia, food allergies, sugar intolerance, hyperglycemia, hypoglycemia, hypertension, kidney disease, adult onset diabetes, liver problems, fibromyalgia, migraine headaches, postmenstrual syndrome, and hyperactivity in children.

A therapeutic agent (or the therapeutic agents) of the present invention are used in a method, kit, combination, and/or composition in a digestive-disorder-effective amount. A "digestive-disorder-effective amount" is intended to qualify the amount of an agent (or agents) required to treat or prevent a digestive disorder in a subject, or relieve to some extent one or more of the symptoms associated with, or related to, a digestive disorder in a subject. In a mammal, this includes, but is not limited to, improving or alleviating the above stated diseases. Such symptoms may include, for example, nausea following a meal, headache prior to or following a meal, a feeling of bloating or tenderness in the rib cage area, bloating, burps or belches, diarrhea, constipation, pain or tenderness in the upper abdomen, and/or nausea relieved by eating or bowel movement.

The term "prevent" or "prevention," in relation to a digestive disorder, means no digestive disorder, condition, or disease development if none had occurred, or no further digestive disorder, condition, or disease development if there had already been development of a digestive disorder, condition, or disease.

When the compositions of the present invention are used in a "digestive-disorder-effective amount" this means that the concentration of the therapeutic agent (or agents) is such that a therapeutic level of agent is delivered over the term that the composition is to be used. Such delivery is dependent on a number of variables including the time period for which the individual dosage unit is to be used, or the flux rate of the therapeutic agent into the gastric fluid or blood serum of the subject. It is understood, however, that specific dose levels of the therapeutic agents of the present invention for any particular subject depends upon a variety of factors including the activity of the specific compound employed, the age, body weight, general health, sex, and diet of the subject, the time of administration, the rate of excretion, the drug combination, and the severity of the particular disorder being treated and form of administration. Treatment dosages generally may be titrated to optimize safety and efficacy. Typically, dosage-effect relationships from in vitro and/or in vivo tests initially can provide useful guidance on the proper doses for subject administration. Studies in animal models generally may be used for guidance regarding effective dosages for treatment of a digestive disorder in accordance with the present invention. In terms of treatment protocols, it should be appreciated that the dosage to be administered will depend on several factors, including the particular agent that is administered, the route administered, the condition of the particular subject, etc. Generally speaking, one will desire to administer an amount of the agent that is effective to achieve a gastric fluid concentration or serum level commensurate with the concentrations found to be effective in vitro. Thus, where an agent is found to demonstrate in vitro activity at, for example, 10 ng/ml of gastric fluid, one will desire to administer an amount of the agent that is effective to provide about a 10 ng/ml concentration in vivo. Determination of these parameters is well within the skill of the art. These considerations, as well as effective formulations and administration procedures, are well known in the art and are described in standard textbooks.

It will also be understood that a digestive-disorder-effective amount of a therapeutic agent of the present invention is dependent, among other things, on the body weight of the subject. Illustratively, where the therapeutic agent is an *Aspergillus oryzae* protease enzyme and the subject is a child or a small animal (for example, a dog), for example, an amount of the enzyme is relatively low in the range of about 500 HUT to about 5,000 HUT is likely to provide gastric fluid concentrations consistent with therapeutic effectiveness. Where the subject is an adult human or a large animal (for example, a horse), achievement of such concentrations of the enzyme are likely to require dose units containing a relatively greater amount of the *Aspergillus oryzae* protease enzyme. For an adult human, a therapeutically effective amount of *Aspergillus oryzae* protease enzyme per dose unit in a composition of the present invention is typically about 8,000 HUT, but can range from about 500 HUT to about 500,000 HUT; a therapeutically effective amount of *Bacillus subtilis* protease enzyme per dose unit in a composition of the present invention is typically about 3,000 PC, but can range from about 750 PC to about 750,000 PC; and a therapeutically effective amount of *Aspergillus niger* lipase enzyme per dose unit in a composition of the present invention is typically about 100 FCCLU, but can range from about 10 FCCLU to about 20,000 FCCLU. For other therapeutic agents of the present invention, an amount of the agent per dose unit can be in a range known to be therapeutically effective for such drugs.

The compositions of the present invention can be administered by any conventional means available for use in conjunction with pharmaceuticals, either as individual therapeutic compounds or as a combination of therapeutic compounds.

The compositions of the present invention include those suitable for oral or buccal (for example, sublingual), or nasogastric administration, although the most suitable route in any given case will depend on the nature and severity of the condition being treated and on the nature of the particular compound which is being used. In one embodiment of the present invention the an *Aspergillus oryzae* protease enzyme, a *Bacillus subtilis* protease enzyme, and an *Aspergillus niger* lipase enzyme are formulated into a capsule dosage form for oral administration.

The pharmaceutical compositions of the present invention can be administered for treating, preventing, or reducing the risk of developing a digestive disorder in a subject by any means that produce contact of these compounds with their site of action in the body, for example in the gastrointestinal fluid or tract of a subject, including the stomach and/or the small intestine, or in the ileum, blood serum, and/or liver of a subject.

The pharmaceutical compositions of the present invention can be administered in dosage forms containing conventional nontoxic pharmaceutically acceptable carriers, excipients, adjuvants, and vehicles as desired.

Adjuvants that can be used in the methods, kits, combinations, and compositions of the present invention include preservatives, wetting agents, or emulsifying agents.

Exemplary preservatives include, for example, methylparaben, propylparaben, phenol, and benzyl alcohol.

Wetting agents and emulsifying agents are well known in the art.

Exemplary excipients include, for example, magnesium stearate, stearic acid, acacia gum, fructose, modified cellulose gum, colloidal silicon dioxide, gelatin, glutens, artificial colors, microcrystalline cellulose, dibasic calcium phosphate, aspartame, and natural flavoring agents.

Carriers may be prepared from a wide range of materials. Without being limited thereto, such materials include diluents, binders and adhesives, lubricants, plasticizers, disintegrants, colorants, bulking substances, flavoring agents, sweeteners and miscellaneous materials such as buffers and adsorbents in order to prepare a particular composition.

Sweetening agents may include, for example, materials such as water-soluble sweetening agents, water-soluble artificial sweeteners, and dipeptide-based sweeteners, including salts thereof and mixtures thereof.

Flavoring agents may include, for example, synthetic flavor oils, and/or oils from plants leaves, flowers, fruits and so forth, and combinations thereof are useful. Non-limiting exemplary flavor oils include spearmint oil, peppermint oil, cinnamon oil, and oil of wintergreen (methylsalicylate). Also useful are artificial, natural, or synthetic fruit flavors such as citrus oils including lemon, orange, grape, lime, and grapefruit, and fruit essences including apple, strawberry, cherry, pineapple, and so forth, without limitation.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders well known to persons skilled in the art.

Exemplary non-limiting solvents include water, ethanol, isopropyl alcohol, methylene chloride, or mixtures and combinations thereof.

Exemplary non-limiting bulking substances include sugar, lactose, gelatin, starch, and silicon dioxide.

Exemplary plasticizers include diethyl phthalate, diethyl sebacate, triethyl citrate, cronotic acid, propylene glycol, butyl phthalate, dibutyl sebacate, caster oil and mixtures thereof, without limitation. The plasticizers may be hydrophobic as well as hydrophilic in nature. Water-insoluble hydrophobic substances, such as diethyl phthalate, diethyl sebacate, and castor oil can be used to delay the release of water-soluble substances.

The skilled artisan will recognize that certain excipients may play multiple roles within any one formulation. For example, corn starch may act as both a filler and disintegrant. The pertinent sections of Remington's The Science and Practice of Pharmacy (2000) relating to carriers, dosage forms and excipients are hereby incorporated herein by reference.

The formulations of the present invention can be administered by any conventional means available for use in conjunction with a dietary supplement or a pharmaceutical drug, either as individual therapeutic compounds or as a combination of therapeutic compounds.

In one embodiment, the pharmaceutical composition of the present invention is administered one to four times a day, or as many times as necessary to achieve the desired therapeutic effect. In another embodiment the composition of the present invention is administered one to four times a day on alternate days. In another embodiment the composition of the present invention is administered in one to about four doses per day on a weekly, biweekly, or monthly basis. In yet another embodiment the composition of the present invention is administered at least about 5 minutes before a meal. In yet another embodiment the composition of the present invention is administered about 20 to about 60 minutes before a meal.

Additionally, the methods, kits, combinations, and compositions of the present invention optionally include a salt, an ester, an amide, an enantiomer, an isomer, a tautomer, a prodrug, or a derivative of an agent of the present invention. Certain compounds of the present invention may exist in different isomeric (for example, enantiomers and diastereoisomers) forms. The invention contemplates all such isomers both in pure form and in admixture, including racemic mixtures. Enol forms are also included.

Certain compounds of the invention also form pharmaceutically acceptable salts, for example, acid addition salts. For example, the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic, and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide, potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. See, for example, S. M. Berge, et al., "Pharmaceutical Salts," J. Pharm. Sci., 66: 1–19 (1977).

Individual enantiomeric forms of compounds of the present invention can be separated from mixtures thereof by techniques well known in the art. For example, a mixture of diastereoisomeric salts may be formed by reacting the compounds of the present invention with an optically pure form of the acid, followed by purification of the mixture of diastereoisomers by recrystallization or chromatography and subsequent recovery of the resolved compound from the salt by basification. Alternatively, the optical isomers of the compounds of the present invention can be separated from one another by chromatographic techniques employing separation on an optically active chromatographic medium.

The therapeutic agents of the present invention can be used alone in a "combination therapy," or used with another therapeutic agent, such as a dietary supplement or pharmaceutical agent that is effective at treating, preventing, or reducing the risk of developing a digestive disorder in a subject, or the symptoms associated with or related to a digestive disorder in a subject in need thereof. The phrase "combination therapy" embraces the administration of an *Aspergillus oryzae* protease enzyme, a *Bacillus subtilis* protease enzyme, and an *Aspergillus niger* lipase enzyme together, or with another therapeutic agent (or combination of agents), such as a dietary supplement or a pharmaceutical agent that is effective at treating, preventing, or reducing the risk of developing a digestive disorder in a subject, or the symptoms associated with or related to a digestive disorder in a subject in need thereof, as part of a specific treatment regimen intended to provide a beneficial effect from the co-action of these therapeutic agents for the treatment of a digestive disorder in a subject. The beneficial effects of the combination include, but are not limited to, pharmacokinetic or pharmacodynamic co-action resulting from the combination of the therapeutic agents. Administration of these therapeutic agents in combination typically is carried out over a defined time period (usually simultaneously, minutes, hours, days, weeks, months, or years depending upon the combination selected). "Combination therapy" generally is not intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, where each therapeutic agent is administered at a different time, as well as administration of these therapeutic agents, or at least two of the therapeutic agents, in a substantially simultaneous manner. Substantially simultaneous administration can be accomplished, for example, by administering to the subject a single tablet or capsule having a fixed ratio of each therapeutic agent or in multiple, single capsules, or tablets, for each of the therapeutic agents. Sequential or substantially simultaneous administration of each therapeutic agent can be effected by any appropriate route. The sequence in which the therapeutic agents are administered is not narrowly critical. "Combination therapy" also can embrace the administration of the therapeutic agents as described above in further combination with other biologically active ingredients, such as, but not limited to, agents for improving the enzymatic or chemical breakdown of ingested food, and with non-drug therapies, such as, but not limited to, surgery.

The therapeutic compounds that make up the combination therapy may be in a combined dosage form or in separate dosage forms intended for substantially simultaneous or sequential administration. The therapeutic compounds that make up the combination therapy may also be administered sequentially, with either therapeutic compound being administered by a regimen calling for two-step administration. Thus, a regimen may call for sequential administration of the therapeutic compounds with spaced-apart administration of the separate, active agents. The time period between the multiple administration steps may range from, for example, a few minutes to several hours to days, depending upon the properties of each therapeutic compound such as potency, solubility, bioavailability, and plasma half-life and kinetic profile of the therapeutic compound, as well as depending upon the effect of food ingestion and the age and condition of the subject. Circadian variation of the target molecule concentration may also determine the optimal dose interval. Examples of suitable pharmaceutically-acceptable formulations containing the therapeutic compounds are given above. Additionally, drug formulations are discussed in, for example, Liberman, H. A. and Lachman, L., Eds., Pharmaceutical Dosage Forms (Marcel Decker, New York, N.Y., 1980). Furthermore, the therapeutic agents of the present invention may be added separately or combined with food before ingestion. When combined, the therapeutic agents are generally combined in bulk with the food before being provided for consumption. When added separately, the therapeutic agents can be in the form of a liquid, solution, or a powder, for example, which is then sprinkled onto or into the food at a predetermined dose. When the therapeutic agents are provided in the form of a powder, the powder may be contained in a capsule, packet, bottle or jar. When the therapeutic agents are provided in the form of a liquid or solution, the liquid or solution may be contained in a capsule, packet, bottle or jar for easy dispensing of the therapeutic agents.

As an optional component, the compositions of the invention can also contain a drug compatible with the digestive enzymes herein described and/or of potentiating the activity of the active ingredients present. These include agents such as anticholinergic drugs, antihistamines, adrenergic, antiulcer, antacids, antidiarrheal, and anti-inflammatory drugs, sedatives, antipyretis, choleretics antirheumatic agents, analgesic drugs, diuretics, antiseptic agents, antilipemic hepatoprotective drugs, and drugs active on gastrointestinal motility (e.g., metoclopramide).

In another embodiment of the present invention, the methods, kits, combinations, and compositions are used with a dietary supplement such as a herb or herbal derivative, including, for example, agrimony, alfalfa, aloe vera, amaranth, angelica, anise, barberry, basil, bayberry, bee pollen, birch, bistort, blackberry, black cohosh, black walnut, blessed thistle, blue cohosh, blue vervain, boneset, borage, buchu, buckthorn, bugleweed, burdock, capsicum, cayenne, caraway, cascara sagrada, catnip, celery, centaury, chamomile, chaparral, chickweed, chicory, chinchona, cloves, coltsfoot, comfrey, cornsilk, couch grass, cramp bark, culver's root, cyani, cornflower, damiana, dandelion, devils claw, dong quai, echinacea, elecampane, ephedra, eucalyptus, evening primrose, eyebright, false unicorn, fennel, fenugreek, figwort, flaxseed, garlic, gentian, ginger, ginseng, golden seal, gotu kola, gum weed, hawthorn, hops, horehound, horseradish, horsetail, hoshouwu, hydrangea, hyssop, iceland moss, irish moss, jojoba, juniper, kelp, lady's slipper, lemon grass, licorice, lobelia, mandrake, marigold, marjoram, marshmallow, mistletoe, mullein, mustard, myrrh, nettle, oatstraw, oregon grape, papaya, parsley, passion flower, peach, pennyroyal, peppermint, periwinkle, plantain, pleurisy root, pokeweed, prickly ash, psyllium, quassia, queen of the meadow, red clover, red raspberry, redmond clay, rhubarb, rose hips, rosemary, rue, safflower, saffron, sage, St. Johns Wart, sarsaparilla, sassafras, saw palmetto, skullcap, senega, senna, shepherd's purse, slippery elm, spearmint, spikenard, squawvine, stillingia, strawberry, taheebo, thyme, uva ursi, valerian, violet, watercress, white oak bark, white pine bark, wild cherry, wild lettuce, wild yam, willow, wintergreen, witch hazel, wood betony, wormwood, yarrow, yellow dock, yerba santa, yucca, and combinations thereof. Herbal derivatives, as used herein, refer to herbal extracts, and substances derived from plants and plant parts, such as leaves, flowers, and roots, without limitation. For example, the herbal or herbal derivative is black cohosh, licorice, false unicorn, siberian ginseng, sarsaparilla, squaw vine, blessed thistle, and combinations thereof.

The use of the term "about" in the present disclosure means "approximately," and use of the term "about" indicates that dosages and amounts outside that cited may also be effective and safe, and such dosages and amounts are also encompassed by the scope of the present claims.

For treatment of a digestive disorder in a subject in need thereof, a composition of the present invention can be used to provide a daily dosage to the subject of at least about 500 HUT *Aspergillus oryzae* protease enzyme, at least about 750 PC *Bacillus subtilis* protease enzyme, and at least about 10 FCCLU *Aspergillus niger* lipase enzyme; or about 500 HUT to about 500,000 HUT *Aspergillus oryzae* protease enzyme, about 750 PC to about 750,000 PC *Bacillus subtilis* protease enzyme, and about 10 FCCLU to about 20,000 FCCLU *Aspergillus niger* lipase enzyme. The daily dose can be administered in one to about four doses per day.

Initial treatment of a digestive disorder can begin with a dose regimen as indicated above. Treatment is generally continued as necessary over a period of a few hours to several days to several weeks to several months or years until the digestive disorder has been controlled or eliminated. Subjects undergoing treatment with a composition of the invention can be routinely monitored by any of the methods well known in the art to determine effectiveness of therapy. Continuous analysis of data from such monitoring permits modification of the treatment regimen during therapy so that optimally effective doses are administered at any point in time, and so that the duration of treatment can be determined. In this way, the treatment regimen and dosing schedule can be rationally modified over the course of therapy so that the lowest amount of the composition exhibiting satisfactory effectiveness is administered, and so that administration is continued only for so long as is necessary to successfully treat the condition or disorder.

In an embodiment of the present invention, the pharmaceutical composition is a tablet, capsule, cachet, lozenge, dispensable powder; powder for suspension, or granule, or packet and is comprised of the dry substances in approximate weights and/or activity units as described below in Table Nos. 1–6:

TABLE NO. 1

| SUBSTANCE | ENZYME ACTIVITY OR AMOUNT PER UNIT |
|---|---|
| *Aspergillus aryzae* protease enzyme | 8,000 HUT |
| *Bacillus subtilis* protease enzyme | 3,000 PC |
| *Aspergillus niger* lipase enzyme | 100 FCCLU |

TABLE NO. 2

| SUBSTANCE | ENZYME ACTIVITY OR AMOUNT PER UNIT |
|---|---|
| Protease *Aspergillus oryzae* | 500 HUT |
| Protease *Bacillus subtilis* | 750 PC |
| Lipase *Aspergillus niger* | 10 LU |

TABLE NO. 3

| SUBSTANCE | ENZYME ACTIVITY OR AMOUNT PER UNIT |
|---|---|
| Protease *Aspergillus oryzae* | 250,000 HUT |
| Protease *Bacillus subtilis* | 375,000 PC |
| Lipase *Aspergillus niger* | 10,000 LU |

TABLE NO. 4

| SUBSTANCE | ENZYME ACTIVITY OR AMOUNT PER UNIT |
|---|---|
| Protease *Aspergillus oryzae* | 500,000 HUT |
| Protease *Bacillus subtilis* | 750,000 PC |
| Lipase *Aspergillus niger* | 20,000 LU |

TABLE NO. 5

| SUBSTANCE | ENZYME ACTIVITY OR AMOUNT PER UNIT |
|---|---|
| Protease *Aspergillus oryzae* | 8,000 HUT |
| Protease *Bacillus subtilis* | 3,000 PC |
| Lipase *Aspergillus niger* | 100 LU |
| Calcium (from Calcium Carbonate) | 300 mg |
| Microcrystalline Cellulose | 500 mg |
| Fructose | 1000 mg |
| Natural Flavor | 250 mg |

TABLE NO. 6

| SUBSTANCE | ENZYME ACTIVITY OR AMOUNT PER UNIT |
|---|---|
| Anylase | 2,000 DU's |
| Protease | 5,000 HUT's |
| Lipase | 100 FCC LU's |

Any suitable antacid can be added to the above formulation in an amount effective to elevate gastric pH.

The International Union of Biochemistry (IUB) classifies the protease from *Aspergillus oryzae* as microbial metallo type proteinase 3.4.24.4.

The International Union of Biochemistry (IUB) classifies the protease from *Bacillus subtilis* as serine type proteinase 3.4.21.14.

The International Union of Biochemistry (IUB) classifies the lipase from *Aspergillus niger* as triacylglycerol acylhydrolase 3.1.1.3. The above formulations may be formulated as solutions, suspensions or emulsions as known in the art.

Methods of isolating and purifying enzymes are well known in the art, and sources of enzymes are readily available from enzyme supplier companies (see, for example, T. Godfrey and S. West editors, Industrial Enzymology (Macmillan Press Ltd, 2$^{nd}$ Edition, 1996).

Toxicity and therapeutic efficacy of the therapeutic agents of the present invention can be determined by standard pharmaceutical procedures, for example, for determining $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The following examples are provided for exemplification of the present invention and are not intended to be limiting in any way.

EXAMPLE 1

Applicants tested the activity of *Aspergillus oryzae* protease in simulated gastric fluid after the addition of varying amounts of calcium carbonate. They found that after nearly 700 mg of calcium carbonate was added to the fluid, the protease activity remained above 75% of optimal activity.

EXAMPLE 2

Applicants tested the activity of *Bacillus subtilis* protease in simulated gastric fluid after the addition of varying amounts of calcium carbonate. They found that after 1200 mg of calcium carbonate was added to the fluid, the protease activity remained above 85% of optimal activity.

EXAMPLE 3

Applicants tested the activity of lipase in simulated gastric fluid after the addition of varying amounts of calcium carbonate. They found that after calcium carbonate was added to the fluid, the lipase activity was not significantly diminished.

The contents of all cited references throughout this application are hereby expressly incorporated by reference. The practice of the present invention will employ, unless otherwise indicated, conventional techniques of food science, pharmacology, and pharmaceutics, which are within the skill of the art.

Although the invention has been described with respect to specific embodiments and examples, it should be appreciated that other embodiments utilizing the concept of the present invention are possible without departing from the scope of the invention. The present invention is defined by the claimed elements, and any and all modifications, variations, or equivalents that fall within the true spirit and scope of the underlying principles.

The invention claimed is:

1. A composition, comprising:
   (a) at least about 500 HUT *Aspergillus oryzae* protease enzyme;
   (b) at least about 750 PC *Bacillus subtilis* protease enzyme; and
   (c) at least about 10 FCCLU *Aspergillus niger* lipase enzyme.

2. The composition of claim 1, further comprising an agent selected from the group consisting of an antacid, a histamine $H_2$ receptor antagonist, and a proton pump inhibitor.

3. The composition of claim 2, wherein the antacid is calcium carbonate.

4. The composition of claim 2, wherein the histamine $H_2$ receptor antagonist is selected from the group consisting of ranitidine, cimetidine, famotidine, nizatidine, and roxatidine acetate.

5. The composition of claim 2, wherein the proton pump inhibitor is selected from the group consisting of omeprazole, lansoprazole, and rabeprazole.

6. The composition of claim 1, wherein the composition further comprises a digestive enzyme selected from the group consisting of a protease, a lipase, an amylase, and a cellulase.

7. The composition of claim 1, wherein the composition comprises about 500 HUT to about 500,000 HUT *Aspergillus oryzae* protease enzyme.

8. The composition of claim 1, wherein the composition comprises about 8,000 HUT *Aspergillus oryzae* protease enzyme.

9. The composition of claim 1, wherein the composition comprises about 750 PC to about 750,000 PC *Bacillus subtilis* protease enzyme.

10. The composition of claim 1, wherein the composition comprises about 3,000 PC *Bacillus subtilis* protease enzyme.

11. The composition of claim 1, wherein the composition comprises about 10 FCCLU to about 20,000 FCCLU *Aspergillus niger* lipase enzyme.

12. The composition of claim 1, wherein the composition comprises about 100 FCCLU *Aspergillus niger* lipase enzyme.

13. The composition of claim 1, wherein the composition is administered orally.

14. The composition of claim 1; wherein the composition is in a dosage form comprising a tablet, capsule, cachet, lozenge, dispensable powder, granule, solution, suspension, or emulsion.

15. A method for treating or reducing the risk of developing a digestive disorder in a subject in need thereof, comprising: administering to the subject a digestive disorder effective amount of a composition which comprises:
  (a) at least about 500 HUT *Aspergillus oryzae* protease enzyme;
  (b) at least about 750 PC *Bacillus subtilis* protease enzyme; and
  (c) at least about 10 FCCLU *Aspergillus niger* lipase enzyme.

16. The method of claim 15, further comprising an agent selected from the group consisting of an antacid, a histamine $H_2$ receptor antagonist, or a proton pump inhibitor.

17. The method of claim 16, wherein the antacid is calcium carbonate.

18. The method of claim 16, wherein the histamine $H_2$ receptor antagonist is selected from the group consisting of ranitidine, cimetidine, famotidine, nizatidine, and roxatidine acetate.

19. The method of claim 16, wherein the proton pump inhibitor is selected from the group consisting of omeprazole, lansoprazole, and rabeprazole.

20. The method of claim 15, wherein the composition further comprises a digestive enzyme selected from the group, consisting of a protease, a lipase, an amylase, and a cellulase.

21. The method of claim 15, wherein the composition comprises about 500 HUT to about 500,000 HUT *Aspergillus oryzae* protease enzyme.

22. The method of claim 15, wherein the composition comprises about 8,000 HUT *Aspergillus oryzae* protease enzyme.

23. The method of claim 15, wherein the composition comprises about 750 PC to about 750,000 PC *Bacillus subtilis* protease enzyme.

24. The method of claim 15, wherein the composition comprises about 3,000 PC *Bacillus subtilis* protease enzyme.

25. The method of claim 15, wherein the composition comprises about 10 FCCLU to about 20,000 FCCLU *Aspergillus niger* lipase enzyme.

26. The method of claim 15, wherein the composition comprises about 100 FCCLU *Aspergillus niger* lipase enzyme.

27. A method for treating or reducing the risk of developing a digestive disorder in a subject in need thereof, comprising: administering to the subject in a combination therapy at least about 500 HUT *Aspergillus oryzae* protease enzyme, at least about 750 PC *Bacillus subtilis* protease enzyme, at least about 10 FCCLU *Aspergillus niger* lipase enzyme, and an agent selected from the group consisting of an antacid, an $H_2$ receptor antagonist and a proton pump inhibitor.

28. The method of claim 27, wherein the antacid is calcium carbonate.

29. The method of claim 27, wherein the histamine $H_2$ receptor antagonist is selected from the group consisting of ranitidine, cimetidine, famotidine, nizatidine, and roxatidine acetate.

30. The method of claim 27, wherein the proton pump inhibitor is selected from the group consisting of omeprazole, lansoprazole, and rabeprazole.

31. The method of claim 27, wherein the composition further comprises a protease, a lipase, an amylase, and a cellulase.

32. The method of claim 27, wherein the composition comprises about 500 HUT to about 500,000 HUT *Aspergillus oryzae* protease enzyme.

33. The method of claim 27, wherein the composition comprises about 8,000 HUT *Aspergillus oryzae* protease enzyme.

34. The method of claim 27, wherein the composition comprises about 750 PC to about 750,000 PC *Bacillus subtilis* protease enzyme.

35. The method of claim 27, wherein the composition comprises about 3,000 PC *Bacillus subtilis* protease enzyme.

36. The method of claim 27, wherein the composition comprises about 10 FCCLU to about 20,000 FCCLU *Aspergillus niger* lipase enzyme.

37. The method of claim 27, wherein the composition comprises about 100 FCCLU *Aspergillus niger* lipase enzyme.

38. The method of claim 27, wherein the *Aspergillus oryzae* protease enzyme, the *Bacillus subtilis* protease enzyme, and the *Aspergillus niger* lipase enzyme are formulated in a single composition.

39. The method of claim 27, wherein the *Aspergillus oryzae* protease enzyme, the *Bacillus subtilis* protease enzyme, and the *Aspergillus niger* lipase enzyme are provided as a separate component of a kit.

40. The method of claim 27, wherein the *Aspergillus oryzae* protease enzyme, the *Bacillus subtilis* protease enzyme, and the *Aspergillus niger* lipase enzyme are administered in a sequential manner.

41. The method of claim 27, wherein the *Aspergillus oryzae* protease enzyme, the *Bacillus subtilis* protease enzyme, and the *Aspergillus niger* lipase enzyme are administered in a substantially simultaneous manner.

42. A pharmaceutical-composition made by combining a digestive-disorder-effective amount of the compound of claim 1 and a pharmaceutically acceptable carrier, excipient, adjuvant, and/or vehicle.

43. A method for making a pharmaceutical composition, comprising: combining a digestive-disorder-effective amount of the compound of claim 1 and a pharmaceutically acceptable carrier, excipient, adjuvant, and/or vehicle.

* * * * *